United States Patent [19]

Rogers et al.

[11] Patent Number: 4,819,649
[45] Date of Patent: Apr. 11, 1989

[54] NONINVASIVE VIBRATION MEASUREMENT SYSTEM AND METHOD FOR MEASURING AMPLITUDE OF VIBRATION OF TISSUE IN AN OBJECT BEING INVESTIGATED

[75] Inventors: Peter H. Rogers, Sandy Springs; Helen M. Cox, Atlanta, both of Ga.

[73] Assignee: Georgia Tech Research Corporation, Atlanta, Ga.

[21] Appl. No.: 926,452

[22] Filed: Nov. 3, 1986

[51] Int. Cl.⁴ .............................................. A61B 10/00
[52] U.S. Cl. .................................. 128/660.02; 73/624; 73/625
[58] Field of Search ...................... 128/328, 660, 24 A, 128/660.02; 73/599, 602, 624, 625, 626, 627, 628, 629, 632, 633

[56] References Cited

U.S. PATENT DOCUMENTS

| | | | |
|---|---|---|---|
| 4,414,850 | 11/1983 | Wiwa et al. | 128/660 |
| 4,543,827 | 10/1985 | Tominaga | 73/599 |
| 4,610,255 | 9/1986 | Shimura et al. | 128/660 |
| 4,653,505 | 3/1987 | Iinuma | 128/660 |

OTHER PUBLICATIONS

Signals and Systems, by Poularikas et al., pp. 219-221, PWS Publisher, 1985.

Primary Examiner—Francis Jaworski
Assistant Examiner—George Manuel
Attorney, Agent, or Firm—Hurt, Richardson, Garner, Todd & Cadenhead

[57] ABSTRACT

A system and method for measuring the acoustically induced vibrations within a living organism. The object is ensonified to set it into low frequency vibration. A continuous wave beam of ultrasonic energy is transmitted along one path and focused at the tissue to be investigated. A focused transducer receives the reflected beam along a second axis such that the intersection of the transmitted and received beams define a small, concentrated region positioned at the object under investigation. The received beam is phase modulated by the amplitude of vibration of the object producing sidebands whose amplitude can be ratioed to the amplitude of the high frequency peak to determine the absolute amplitude of the low frequency vibration.

9 Claims, 3 Drawing Sheets

RESPONSE OF GOLDFISH OTOLITHS AT 200 Hz

RESPONSE OF GOLDFISH OTOLITHS AT 600 Hz

RESPONSE OF GOLDFISH OTOLITHS AT 1000 Hz

NONINVASIVE VIBRATION MEASUREMENT SYSTEM AND METHOD FOR MEASURING AMPLITUDE OF VIBRATION OF TISSUE IN AN OBJECT BEING INVESTIGATED

STATEMENT OF GOVERNMENT INTEREST

This invention was made with Government support under Contracts No. N00014-84-K-0164 and No. N61331-85-D-0025 awarded by the Department of the Navy. The Government has certain rights in the invention.

BACKGROUND OF THE INVENTION

The invention herein disclosed and claimed is directed to the use of continuous wave (cw) frequency energy of high spectral purity in the fluid-coupled accurate measurement of the amplitude of low frequency vibration of an object or entity under investigation. In the description which follows, the invention will be described in conjunction with the accurate measurement of the amplitude of acoustically induced vibration of organs in a living fish, in which the living organism and the ultrasonic investigating mechanism are all coupled underwater, but it will be apparent to those skilled in the art that other and different applications may be made of the invention without departing from the principles disclosed herein.

In the field of measuring the amplitude of acoustically induced vibrations within a living organism, there is currently no technique available for use which does not at least require surgery. In fact, certain available techniques cannot be performed on living organisms. For the purpose of the description which follows, currently available techniques which require surgery or which cannot be performed on living organisms will be termed "invasive" techniques. In distinction, a technique which does not require surgery and which may be performed on a living organism will be termed "non-invasive". Invasive techniques or methods include the use of the Mossbauer effect, lasere vibrometry and holography and the use of accelerometers or microphones.

The invasive techniques involve surgery to expose the tissue to be investigated and, in the case of those employing the Mossbauer effect or of the use of accelerometers, the probe is required to be placed in contact with the tissue being investigated, which will invariably alter its vibrational characteristics. For the purpose of this description, a method which alters the vibrational characteristics of the organism and its tissue will be termed an "intrusive" technique, whereas a technique which does not alter the vibrational characteristics will be termed as "non-intrusive".

BRIEF SUMMARY OF THE INVENTION

Of principal concern in connection with the invention is the provision of a method and apparatus for non-invasive, non-intrusive investigations within a living organism.

It is also of concern to provide apparatus and method whereby accurate amplitude measurement of low frequency vibration of an object is made possible through the use of phase modulation, effected by virtue of the acoustical path variation due to the vibration of the object, of continuous wave energy which is focused or concentrated upon the object and reflected or scattered thereby.

In another aspect, the invention involves transmitting a beam of ultrasonic continuous wave energy along one axis, receiving a beam of reflected ultrasonic energy along a second axis, intersecting the axes of the transmitted and received beams where the intersecting beams define a small concentrated spot, relatively positioning a vibrating object under investigation and the concentrated spot so that the receiving beam is modulated by the vibration of the object, and determining the amplitude of vibration of the object from the modulation of the received beam. Specifically, the amplitude of vibration may be determined by ratioing the amplitudes of sidebands resulting from modulation to the amplitude of the phase carrier in the received beam.

Basically, the objectives of the invention are achieved by focusing or concentrating continuous wave ultrasonic energy on an object which is vibrating at a low frequency, detecting the energy scattered or reflected by the object and determining the amplitude of low frequency vibration of the object from the modulation caused by the low frequency vibrational movement of the object. Since the ultrasonic energy is of continuous wave form, the modulation is of double sideband form and the determination of the amplitude of vibration involves measurement of the ratio of sideband amplitude to the amplitude of the ultrasonic frequency.

These and other objects of the invention will become more apparent as this description proceeds.

BRIEF DESCRIPTION OF THE DRAWING FIGURES

DETAILED DESCRIPTION

Figure 1:
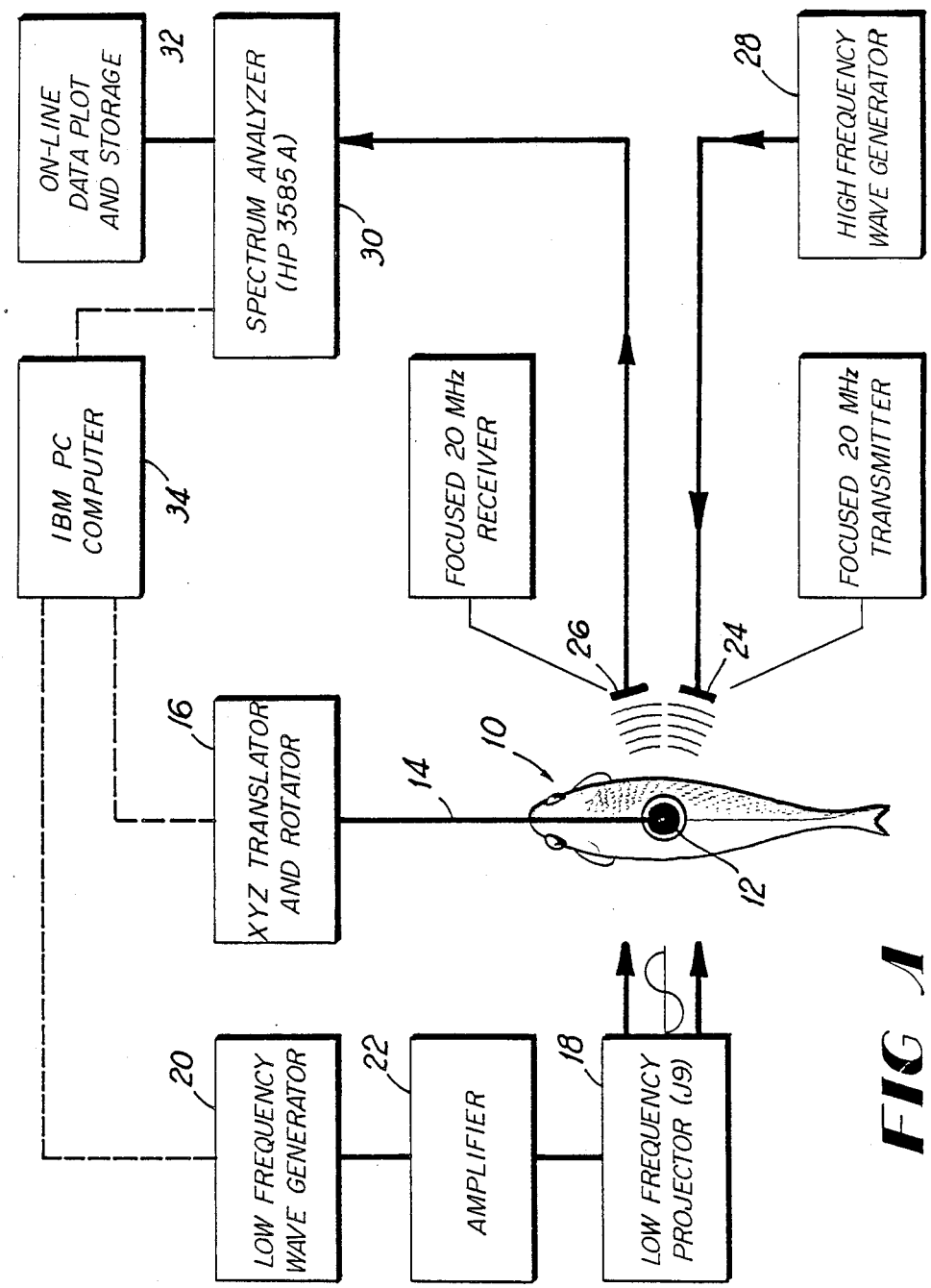
FIG. 1 is a schematic view illustrating a preferred system according to this invention.

Referring to FIG. 1, the schematic representation therein illustrates the physical arrangement utilized to measure, in vivo, vibratory amplitudes of auditory organs of goldfish in accord with this invention. The specimen, properly anesthetized, is indicated by the reference character 10 and is held in position by a clamping device 12 carried by the arm 14 of a translator 16. The details of the translator form no part of this invention but the mechanism should be capable of both linear translation of the specimen along any one or all of the orthogonal axes X, Y and Z and the rotation of the specimen about one of these axes. In the particular embodiment shown, the Z axis is perpendicular to the plane of the drawing and rotation about this axis may be effected. The specimen is ensonified by an underwater sound projector 18 (Naval Research Lab's J9) at a frequency within the auditory range of the specimen (approximately 100–1000 Hz), the low frequency wave generator 20 being connected through the amplifier 22 to the projector 18. A convergent beam of continuous wave ultrasonic energy is produced by the low power (0.1 watt) transducer or transmitter 24, the beam being focused at a spot within the specimen, and a second, receiving transducer 26 is also focused on this same spot to receive the divergent beam of energy reflected (or scattered) by the organ or tissue upon which the beams are focused. The transmitter 24 and receiver 26 are both ¼ inch diameter, spherically focused, immersion type 20 MHz piezoelectric transducers with a 1¼ inch focal length (made by Panametrics, Inc.). These transducers are focused at the same point at their focal length with the two beams crossing at approximately 20° to produce a spot size of about r=0.25 mm and z=0.80 mm, where r is the transverse radius of the spot and z is the depth thereof. This provides sufficient spatial resolution to resolve the goldfish organs of interest.

The specimen, transducers and sound wave projector are most conveniently located underwater to provide the most beneficial fluid coupling. The transmitter is connected to a high frequency wave generator 28 whereas the receiver 26 outputs to the spectrum analyzer 30 (HP 3585A) having sufficient dynamic range (e.g., in excess of 80 dB). An on-line data plotter and storage device 32 is connected to the spectrum analyzer 30 and the analyzer, translator and low frequency wave generator are all connected to the personal computer 34 for effecting the necessary arithmetic operations on the outputs from the analyzer and for effecting the desired frequency outputs from the wave generator 20 and the desired movements of the specimen as achieved by the translator.

The use of cw ultrasonic energy concentrated upon a small organ being investigated or a small area of tissue being investigated, when that organ or tissue is vibrating at some low frequency, causes modulation of the reflected or scattered ultrasonic energy which may be utilized to determine the amplitude of vibration of the subject matter of interest. In the case of the auditory organs of fish, the information provides knowledge heretofore unknown, but it will be readily apparent to those of skill in the art that other and different uses may be made of the invention. For example, non-invasive and non-intrusive investigation of tissue within a living organism, which tissue is of the type known to display a particular amplitude of vibration when excited at a particular low frequency, may be used to determine the viability of such tissue. As another example, the invention provides means whereby the size, density and composition of kidney stones may be investigated without requiring surgery. It should also be recognized that the body being investigated need not be stimulated with a low frequency sound field as herein, but may be excited into vibration at the required frequency by supporting the body and shaking or vibrating the support. Nor is it a prerequisite that the body be immersed in water or similar liquid, since the transmitter and receiver may simply be provided with suitable liquid coupling to the body. As to this latter, the transducers may be submerged in water in a sealed container having a flexible diaphragm which is brought into contact with the body, with or without the use of a coupling gel or the like.

The requirement for an ultrasonic source of high spectral purity is important in obtaining accurate measurements.

It can be shown that the modulation is double sideband modulation on the carrier (ultrasonic) frequency, and that the vibrational amplitude of the tissue under investigation can be determined from the ratio of the amplitude of the sidebands to the amplitude of the carrier as read from the analyzer and an absolute value of the vibration amplitude is obtained.

Figure 2:
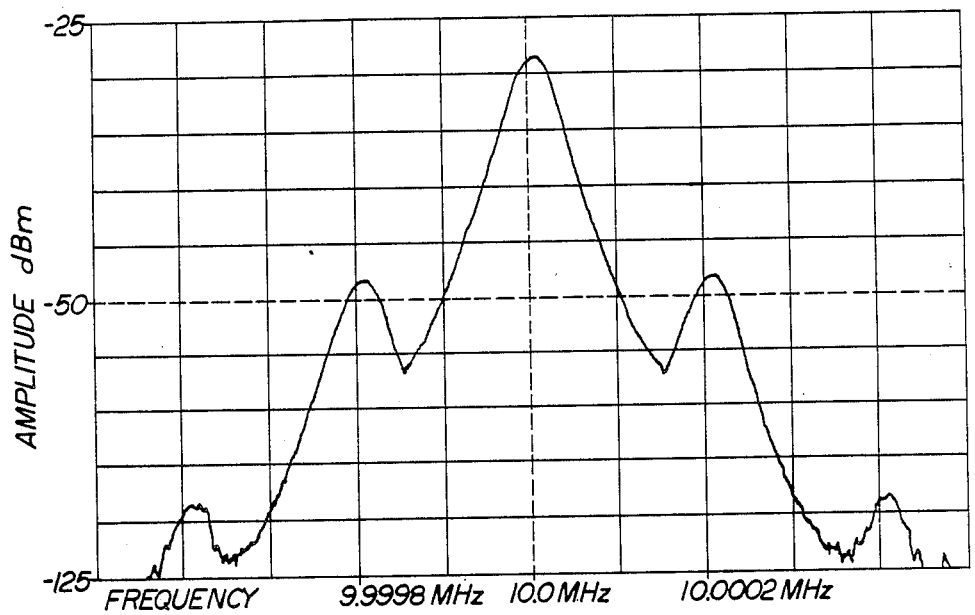
FIGS. 2 through 4 are graphs indicating the responses of auditory organs of goldfish when exposed to different frequencies within their audible range.
Figure 3:
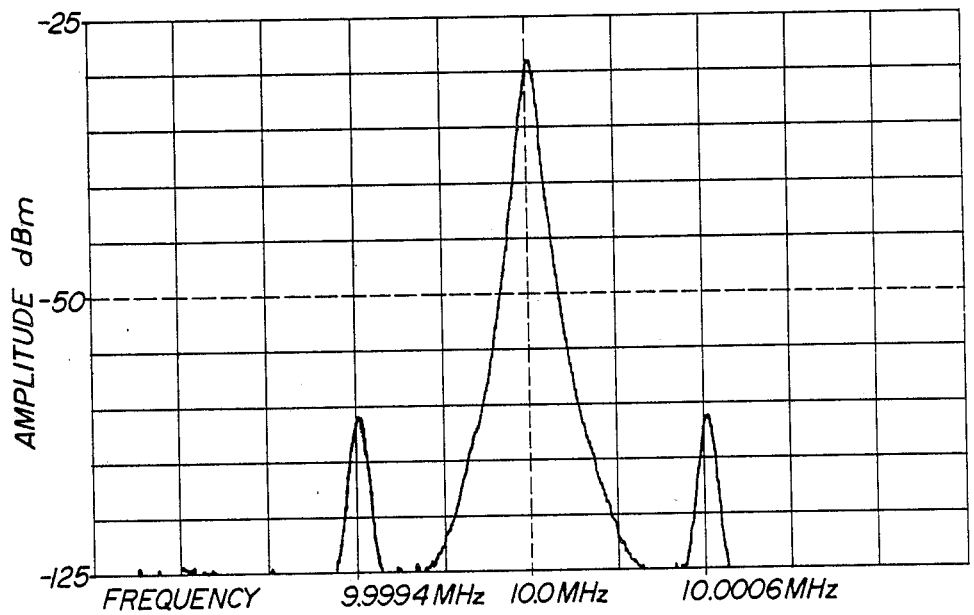
Figure 4:
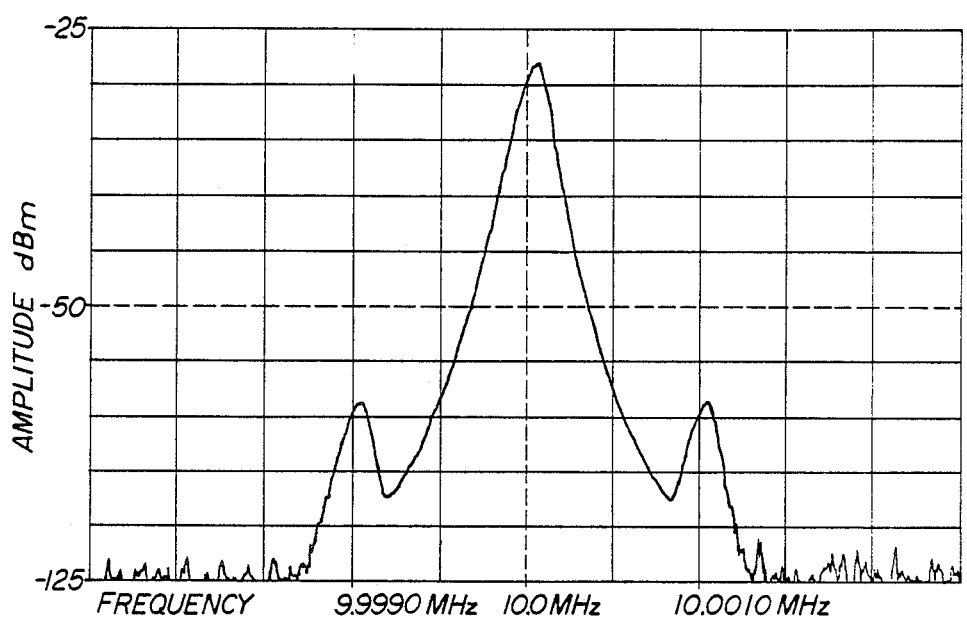

FIGS. 2–4 illustrate echos from goldfish otoliths at 200, 600 and 1000 Hz excitation frequencies and probed with 10 MHz ultrasonic frequency. Each graph illustrates the carrier echo frequency amplitude response C as well as the amplitudes SB1 and SB2 of the two sidebands. The auditory organs under consideration are of about 1 mm height and width. Amplitudes of vibration of goldfish otoliths as measured and corresponding to the graphs of FIGS. 2-4 respectively were 2.7, 0.17 and 0.25 $10^{-7}$m.

We claim:

1. The method of investigating an acoustically vibrating object which comprises the steps of obtaining an acoustically vibrating object, transmitting a focused beam of ultrasonic continuous wave energy along one axis into the object, receiving a focused beam of reflected ultrasonic energy along a second axis from the object, intersecting the axes of the transmitted and received beams such that the beams at the intersection of their axes define a small, concentrated spot within the object, relatively positioning the object under investigation and the concentrated spot so that the received beam is phase modulated by the vibration of the object, the modulated received beam including a carrier and sidebands and determining the amplitude of vibration of the object from the phase modulation of the received beam.

2. The method as defined in claim 1 wherein the step of determining the amplitude of vibration of the object includes comparing the amplitudes of sidebands resulting from phase modulation to the amplitude of the carrier in the received beam.

3. The method of investigating a vibrating entity with ultrasonic energy which comprises the steps of focusing continuous wave ultrasonic energy on the entity, receiving continuous wave ultrasonic energy reflected or scattered by the entity, and determining the amplitude of vibration of the object from the phase modulation of the received energy as phase modulated by the vibration of the object.

4. Apparatus for investigating a particular volume within a living organism which comprises the combination of:
 means for non-invasively illuminating the particular volume within the living organism with continuous wave ultrasonic energy;
 means for vibrating the living organism including the particular volume being investigated at a frequency which causes vibration of the particular volume being investigated to phase modulate the continuous wave ultrasonic energy returned from the particular volume being investigated;
 means for determining the amplitude of vibration of the particular volume being investigated from the phase modulated continuous wave untrasonic energy.

5. Apparatus as defined in claim 4 wherein said means for determining the amplitude of vibration includes means for comparing the amplitude of upper and lower sidebands to the amplitude of the continuous wave ultrasonic energy.

6. The method of investigating the amplitude response of living tissue of a living organism to an excitation frequency which causes acoustic vibration of the living tissue being investigated, which comprises the steps of:
 subjecting the living organism to the excitation frequency;
 focusing continuous wave ultrasonic energy on the living tissue being investigated so that the living tissue being investigated reflects or scatters ultrasonic energy which is phase modulated by vibrational movement of the living tissue being investigated;

determining the amplitude of the vibration of the living tissue being investigated from the reflected or scattered continuous wave ultrasonic energy.

7. The method of investigating tissue of a living organism which comprises the steps of:
   vibrating the living organism at an excitation frequency which causes vibration of the tissue being investigated;
   focusing low power ultrasonic energy on the tissue being investigated by coupling such ultrasonic energy to the living organism through a liquid medium, the frequency of the ultrasonic energy being a continuous wave form so that the continuous wave ultrasonic energy reflected or scattered from the tissue being investigated is phase modulated by the vibration of the tissue being investigated to produce upper and lower sidebands generally centered on the frequency of the ultrasonic energy;
   detecting, through the liquid medium, the phase modulated energy reflected or scattered from the tissue being investigated; and
   determining the amplitude of vibration of the living tissue being investigated from the ratio of the amplitude of the upper and lower sidebands to the amplitude of the continuous wave frequency of the detected ultrasonic energy.

8. Apparatus for investigating the amplitude response of living tissue of a living organism to an excitation frequency which causes vibration of the living tissue being investigated, which comprises the combination of:
   means for subjecting the living organism to an excitation frequency which causes vibration of the living tissue being investigated;
   means for focusing continuous wave ultrasonic energy on the living tissue being investigated so that the living tissue being investigated reflects or scatters ultrasonic energy phase modulated by vibrational movement of the living tissue being investigated; and
   means for determining the amplitude of the vibration of the living tissue being investigated from the reflected or scattered ultrasonic energy.

9. The method of investigating a particular region of living tissue of a living organism, which comprises the steps of:
   ensonifying the living organism with low frequency acoustic energy having a spectrum including a frequency which causes the particular region to vibrate;
   focusing continuous wave ultrasonic energy on the particular region of the living tissue in which the focused continuous wave energy is of a frequency sufficiently high so that vibration of the particular region of the living tissue is substantially unaffected thereby;
   detecting the continuous wave ultrasonic energy on the particular region of the living tissue in which the focused continuous wave energy is of a frequency sufficiently high so that vibration of the particular region of the living tissue is substantially unaffected thereby;
   detecting the continuous wave ultrasonic energy reflected or scattered by the particular region as phase modulated by the vibrational movement of the particular region of the living tissue; and
   determining the amplitude of vibration of the particular region of the living tissue from the detected continuous wave ultrasonic energy as phase modulated by the vibrational movement of the living tissue.

* * * * *